United States Patent [19]

Bock et al.

[11] Patent Number: 5,026,703

[45] Date of Patent: Jun. 25, 1991

[54] PEPTIDE OXYTOCIN ANTAGONISTS

[75] Inventors: Mark G. Bock, Hatfield; Roger M. Freidinger, Lansdale; Robert M. DiPardo, Lansdale, all of Pa.

[73] Assignee: Merck & Co., Inc., Rahway, N.J.

[21] Appl. No.: 535,816

[22] Filed: Jun. 11, 1990

[51] Int. Cl.[5] .................. C07D 521/00; A61K 31/50
[52] U.S. Cl. .................. 514/247; 540/460; 514/183
[58] Field of Search .................. 514/247; 540/460

[56] References Cited
U.S. PATENT DOCUMENTS
4,900,818 2/1990 Czech .................. 546/460

*Primary Examiner*—Robert T. Bond

*Attorney, Agent, or Firm*—Frank P. Grassler; Charles M. Caruso; Richard S. Parr

[57] ABSTRACT

Peptide compounds of formula I are antagonists of oxytocin and are useful in the treatment of preterm labor and dysmenorrhea, and for the stoppage of labor prepatory to Caesarian delivery.

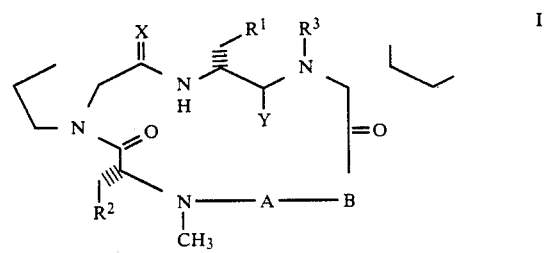

8 Claims, No Drawings

PEPTIDE OXYTOCIN ANTAGONISTS

BACKGROUND OF THE INVENTION

This invention pertains to the field of obstetrics.

In the field of obstetrics, one of the most important problems is the management of preterm labor. A significant number of the pregnancies progressing past 20 weeks of gestation experience premature labor and delivery which is a leading cause of neonatal morbidity and mortality.

It has recently been proposed that a selective oxytocin antagonist would be the ideal tocolytic agent. In the last few years, evidence has accumulated to suggest strongly that oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part by a well-documented increase in the number of oxytocin receptors in this tissue. This 'up-regulation' of oxytocin receptors and enhanced uterine sensitivity appears to be due to trophic effects of rising plasma levels of estrogen towards term. By blocking both the direct (contractile) and indirect (enhanced prostaglandin synthesis) effects of oxytocin on the uterus, a selective oxytocin antagonist would likely be more efficacious for treating preterm labor than current regimens. In addition, since oxytocin at term has major effects only on the uterus, such a compound would be expected to have few, if any, side effects.

The compounds of the present invention may also be useful for the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist may be more efficacious for treating dysmenorrhea than current regimens.

An additional use for the present invention is for the stoppage of the labor prepatory to Caesarian delivery.

It was, therefore, a purpose of this invention to identify substances which more effectively antagonize the function of oxytocin in disease states in animals, preferably mammals, especially in humans. It was another purpose of this invention to prepare novel compounds which more selectively inhibit oxytocin. It was still another purpose of this invention to develop a method of antagonizing the functions of oxytocin in disease states in mammals. It is also a purpose of this invention to develop a method of preventing or treating oxytocin related disorders of particularly preterm labor and dysmenorrhea.

SUMMARY OF THE INVENTION

It has now been found that compounds of Formula I are antagonists of oxytocin and bind to the oxytocin receptor. These compounds are useful in the treatment and prevention of oxytocin-related disorders of animals, preferably mammals and especially humans. These disorders are primarily preterm labor and dysmenorrhea. The compounds would also find usefulness for stoppage of labor prepatory to Caesarian delivery.

DETAILED DESCRIPTION OF THE INVENTION

The compounds of the present invention are of the formula:

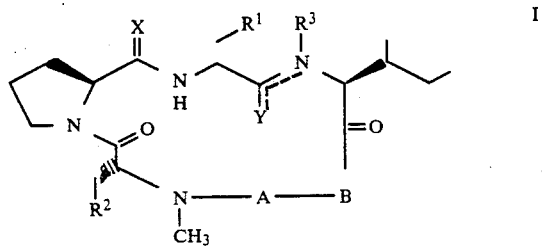

wherein:

A is 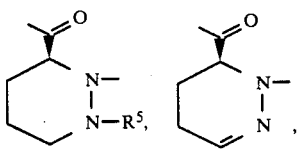

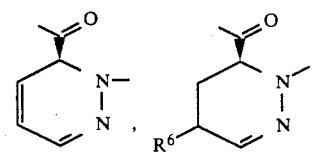

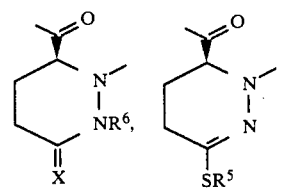

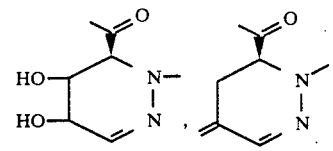

B is 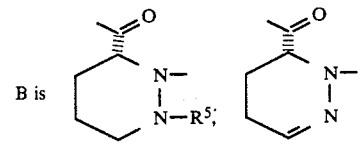

$R^1$ and $R^2$ are the same and are cyclohexyl or phenyl;

$R^3$ is hydrogen, $C_{1-4}$alkyl, or acetyl, when Y is O, S, or $H_2$ for

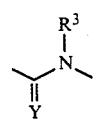

or $R^3$ is absent when Y is S—$C_{1-4}$alkyl or $SCH_2CO_2R^4$ for

$R^4$ is hydrogen, $C_{1-4}$ straight or branch chained alkyl;
$R^5$ is hydrogen except when attached to S, $C_{1-4}$alkyl, $CH_2CO_2R^4$;
$R^6$ is

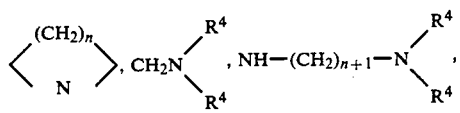

or $CH(CO_2R^4)_2$, where $R^4 \neq H$ and n is 1–4;

X is O or S;

Y is O, S, $H_2$, S—$C_{1-4}$alkyl or S—$CH_2$—$CO_2R^4$; and the pharmaceutically acceptable salts thereof.

Preferably, $R^3$ is hydrogen; $R^4$ is methyl or ethyl; $R^5$ is hydrogen except when attached to S, or methyl; and Y is O, S, or $H_2$.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula I.

The ability of the compounds of Formula I to antagonize oxytocin makes these compounds useful as pharmaceutical agents for mammals, especially for humans, for the treatment and prevention of disorders wherein oxytocin may be involved. Examples of such disorders include preterm labor and especially dysmenorrhea. These compounds may also find usefulness for stoppage of labor prepatory to Caesarian delivery. Because of the known relationships of vasopressin to oxytocin, the compounds of the present invention are also useful as vasopressin antagonists. They are useful in the treatment or prevention of disease states involving vasopressin disorders.

The compounds of Formula I may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal and subcutaneous.

For oral use of an antagonist of oxytocin according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of oxytocin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 2 mg/kg to about 10 mg/kg of body weight administered in single or divided doses. In some cases, however, it may be necessary to use dosages outside these limits.

The compounds of Formula I are prepared according to the following schemes

5,026,703
SCHEME 1
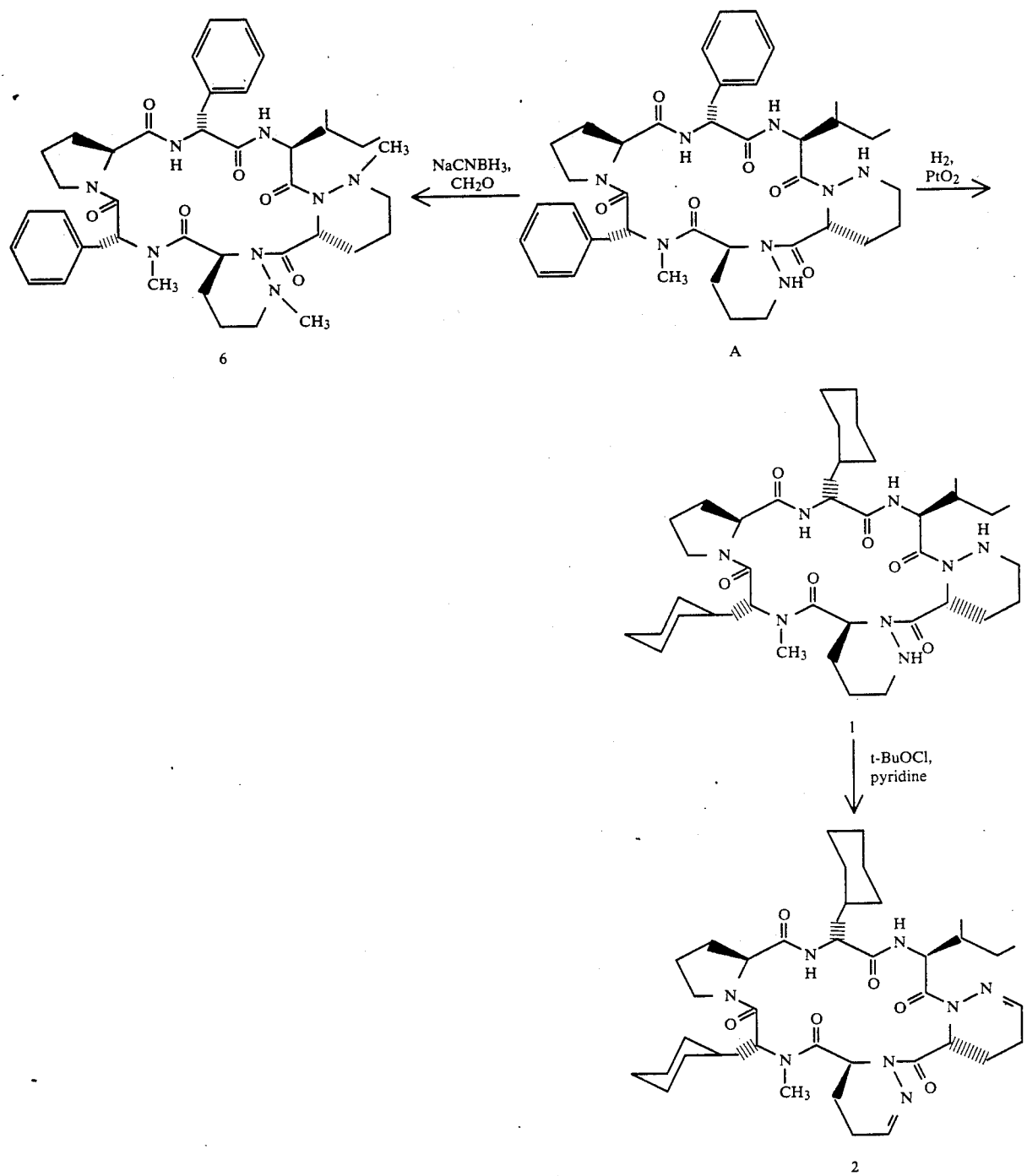

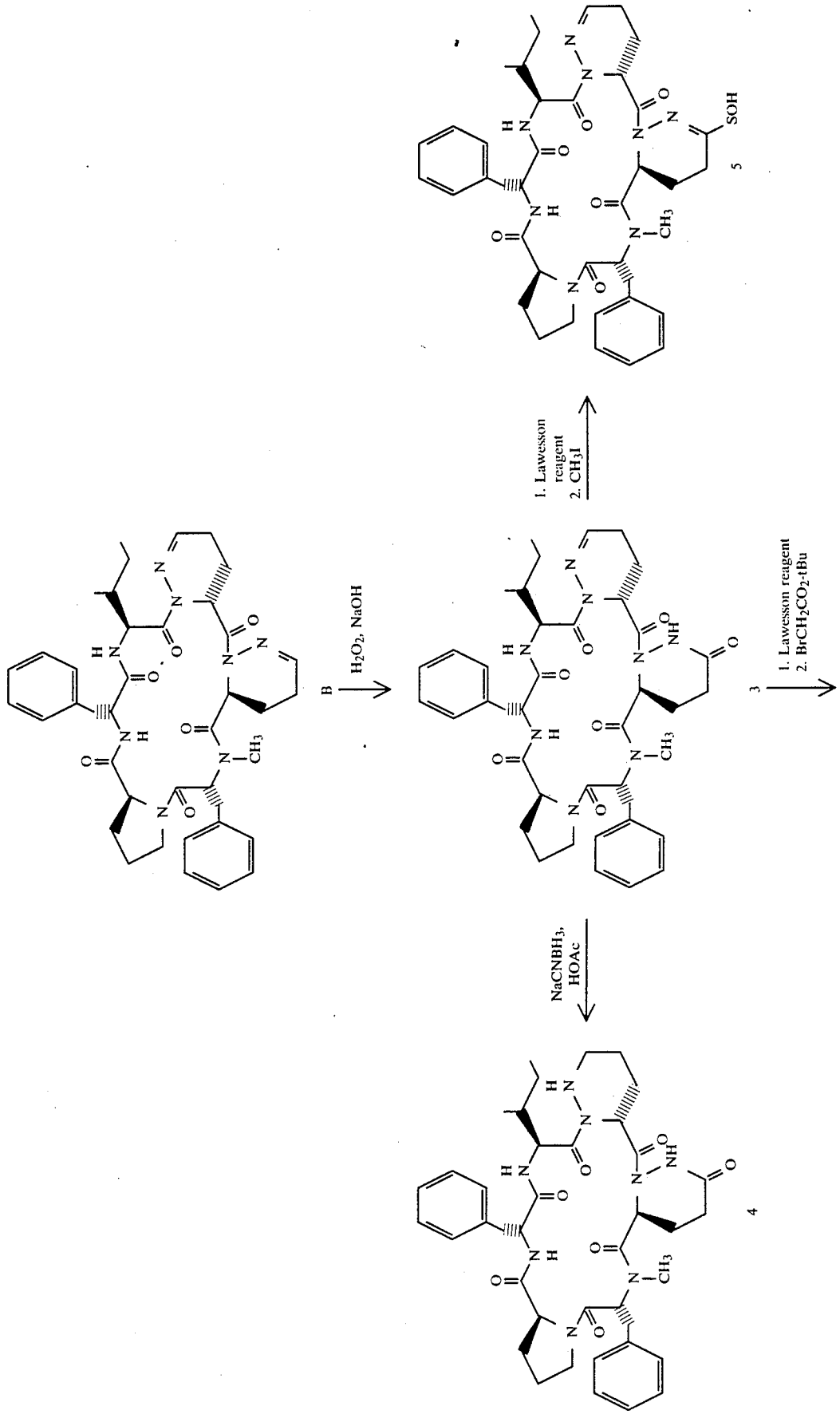
SCHEME 2

-continued
SCHEME 2
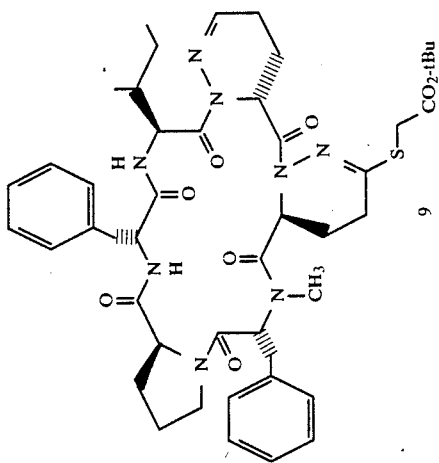
9

SCHEME 3
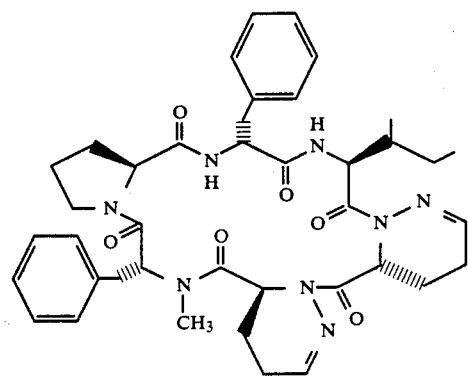
↓ DDQ, PhH
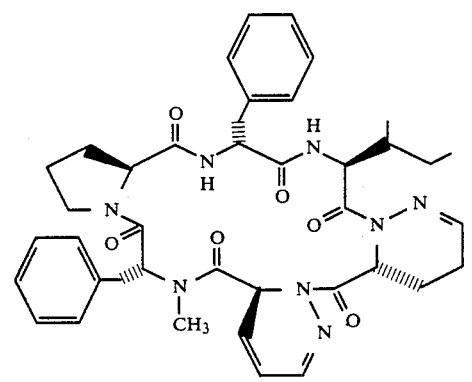
8
OsO₄, pyridine →
-continued
SCHEME 3
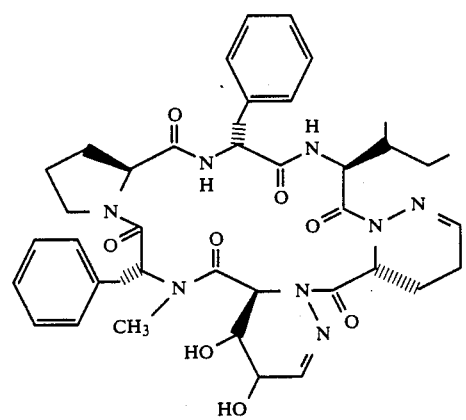
13
↓ NaCNBH₃
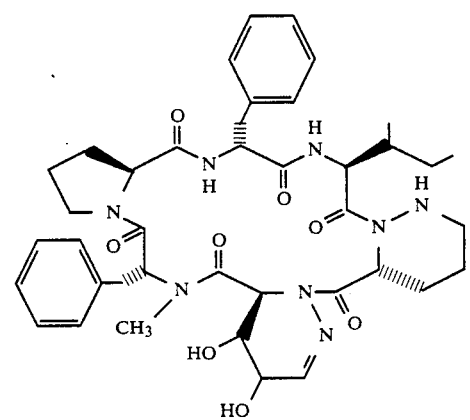
14

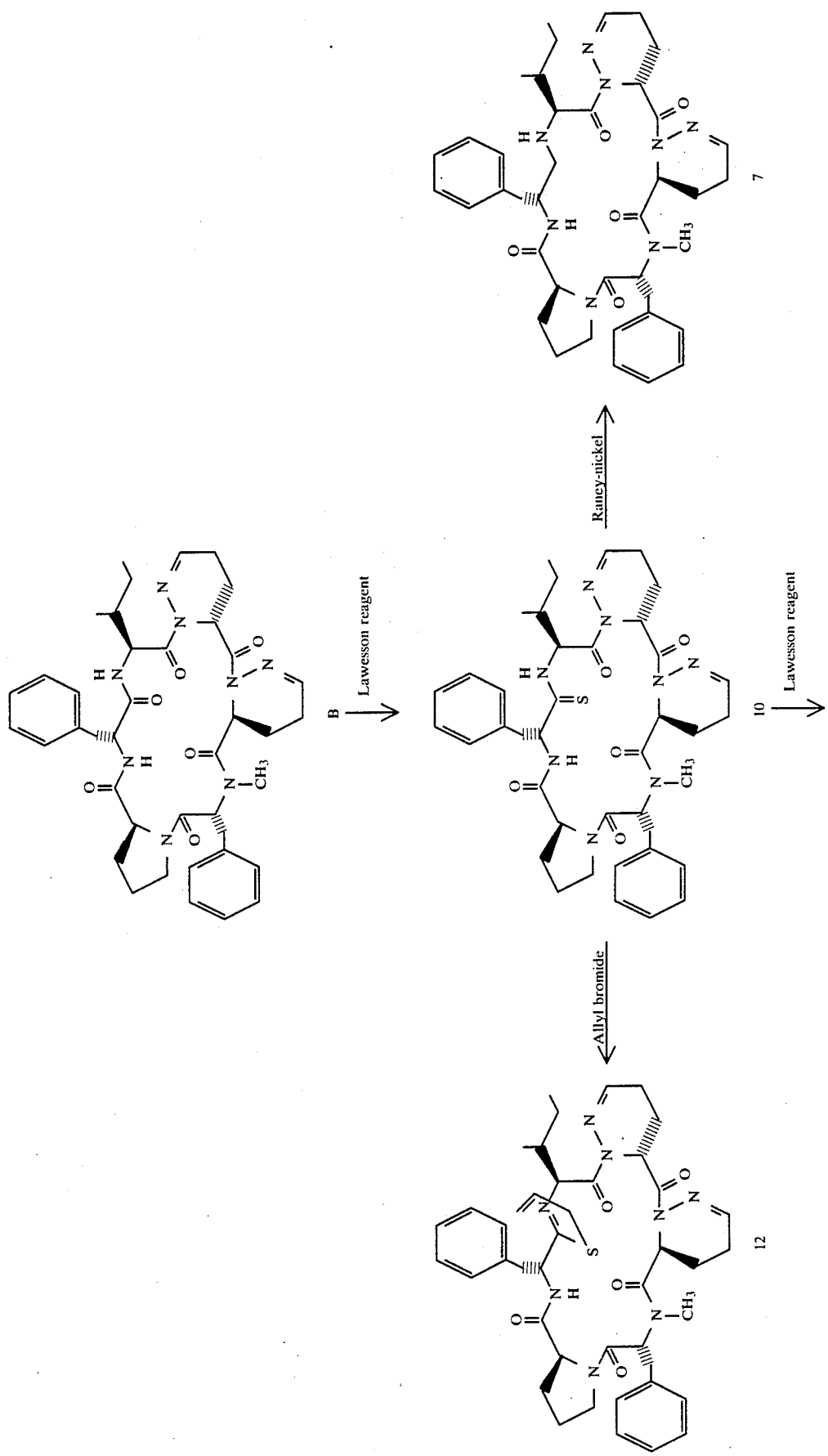
SCHEME 4

-continued
SCHEME 4
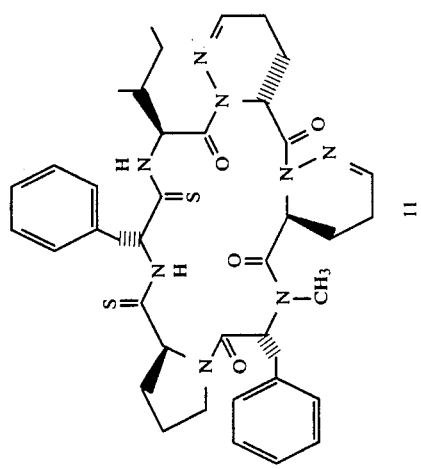
11

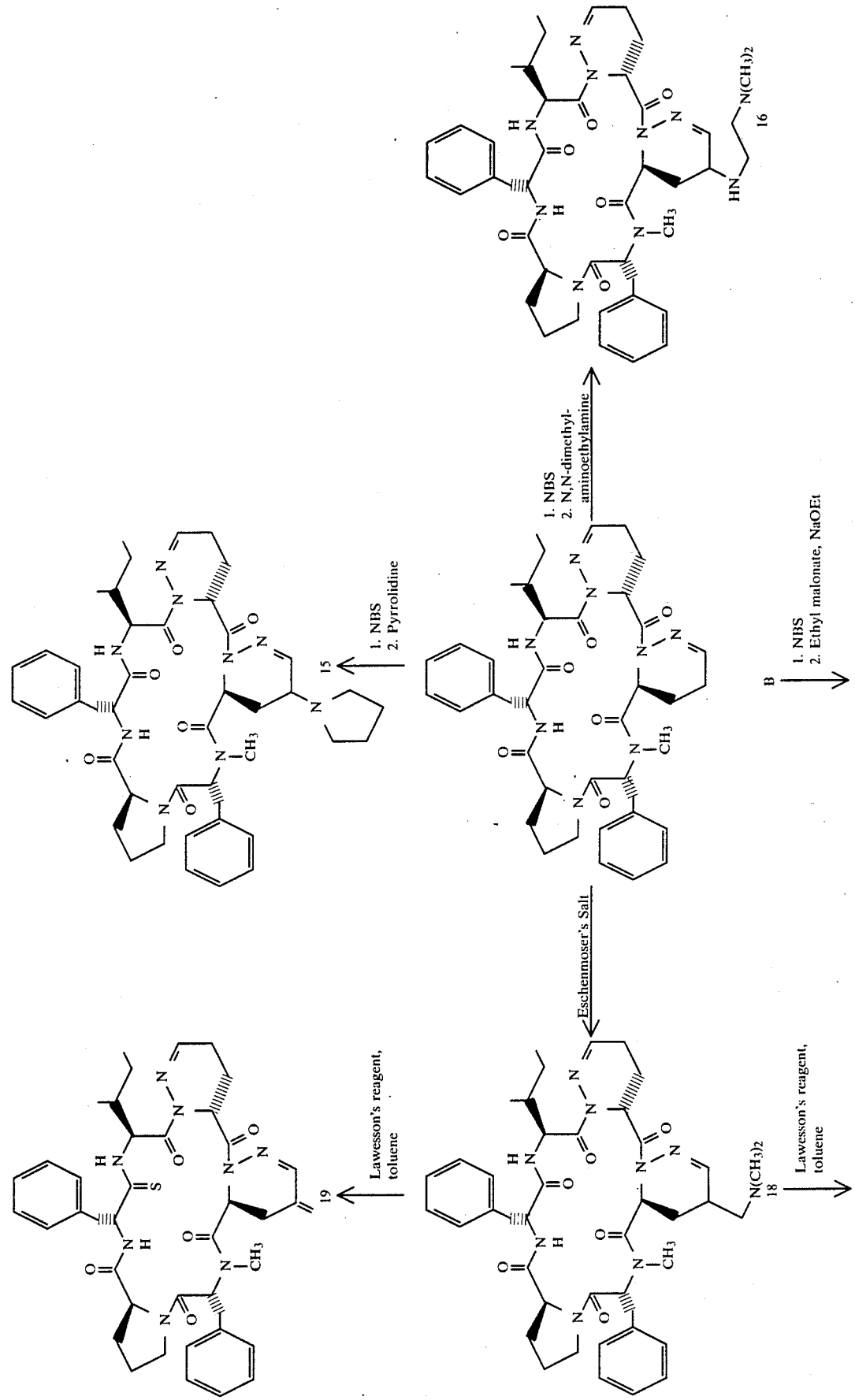

-continued
SCHEME 5
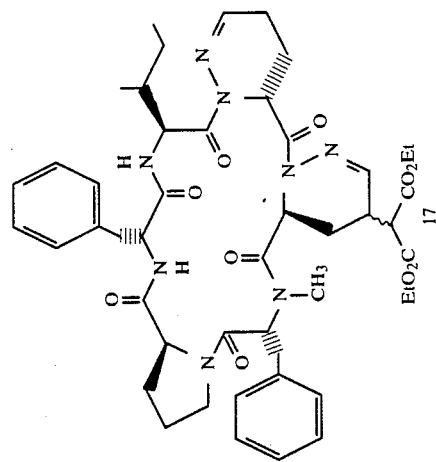
17
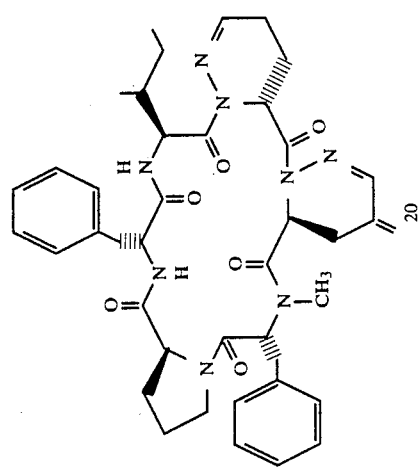
20

The phenyl rings in the cyclic hexapeptide are selectively reduced (Scheme 1) at ambient temperature with hydrogen gas, in a suitable solvent such as ethanol and in the presence of a catalyst, preferably platinum oxide to give 1. The product 1 is then oxidized at ambient temperature with N-chlorosuccinimide in methylene chloride, or with Fremy's salt in a water-methanol mixture, or with sodium hypochlorite in pyridine to give 2. The transformation of 1 to 2 is preferentially carried out with tert-I butylhypochlorite as oxidizing reagent in a solvent such as pyridine at 0° C. for 60 minutes. To give compounds of the formula I, compound A can also be reductively alkylated. Accordingly, treatment of A with formaldehyde solution in glacial acetic acid in the presence of the requisite amount of sodium cyanoborohydride yields 6.

Compounds of the formula I can also be obtained by oxidizing the piperazic acid moieties in compound B with alkaline hydrogen peroxide (Scheme 2). The product 3 is then selectively reduced with triethyl silane in trifluoroacetic acid or preferentially with sodium cyanoborohydride in glacial acetic acid to yield 4. Alternatively, compound 3 is reacted with the Lawesson reagent in toluene at ambient temperature to afford an intermediate thioamide which is alkylated, in the presence of a phase transfer catalyst such as tetra-n-butylammoniumhydrogen sulfate, with methyl iodide to give 5 or with tert-butylbromoacetate to afford 9.

Dehydrogenation of compound B (Scheme 3) with 2,3-dichloro-5,6-dicyano-1,4-benzoquinone in benzene at the refluxing temperature of the solvent yields compound 8. This material is bis-hydroxylated at ambient temperature with osmium tetroxide in a pyridine/toluene solvent mixture to afford the diol 13. The product 13 is then reduced in glacial acetic acid with sodium cyanoborohydride giving 14.

Treatment of compound B in toluene with the Lawesson reagent transforms it to the monothioamide 10 (Scheme 4). Further reaction of 10 with the Lawesson reagent affords the dithioamide 11. Product 10 is desulfurized with freshly prepared Raney-nickel catalyst in a suitable solvent such as ethanol or acetone to give 7. The thioamide 10 can also be selectively alkylated on sulfur with alkylating agents, such as allyl bromide, in the presence of a phase transfer calalyst like tetra-n-butylammonium sulfate, to yield 12.

Irradiation of the cyclic hexapeptide B with a sunlamp in a suitable solvent such as carbon tetrachloride and in the presence of N-bromosuccinimide affords a bromopiperazic acid intermediate (Scheme 5). This intermediate bromo compound, when reacted with nucleophilic reagents in an appropriate solvent, gives products in which the bromine atom has been replaced by the nucleophile. For example, reaction of the bromo compound in tetrahydrofuran with pyrrolidine gives 15, reaction with N,N-dimethylaminoethylamine yields 16, and reaction with sodium diethyl malonate in ethanol affords 17. Alternatively, when compound B is reacted in tetrahydrofuran with N,N-dimethylmethyleneammonium iodide (Eschenmoser's salt) in the presence of an acid catalyst like camphorsulfonic acid there is obtained the dimethylaminomethyl compound 18. Heating this product in toluene with the Lawesson reagent results in elimination of dimethylamine to give 20 and in the conversion of the isoleucine-phenylalanine amide group to the corresponding thioamide group to give 19.

The invention is further defined by reference to the following examples, which are intended to be illustrative and not limiting.

All temperatures are in degrees Celsius.

EXAMPLE 1 cyclo-[D-3-Cyclohexylalanyl-L-isoleucyl-D-hexahydro-3-pyridazinecarbonyl-L-hexahydro-3-pyridazinecarbonyl-3-cyclohexyl-N-methyl-D-alanyl-L-prolyl]

To a solution of 20 ml of ethanol in a small pressure bottle containing 95 mg of cyclo-[D-phenylalanyl-L-isoleucyl-D-hexahydro-3-pyridazinecarbonyl-L-hexahydro-3-pyridazinecarbonyl-N-methyl-D-phenylalanyl-L-prolyl] was added 100 mg of platinum oxide catalyst. The suspension was hydrogenated at room temperature using a Parr apparatus at 50 psi for 27 hours. The reaction mixture was filtered through Celite and the filtrate was concentrated to afford the crude product as a glassy oil. Preparative thick layer chromatography on silica gel (2 mm plate thickness) using chloroform-methanol-concentrated ammonium hydroxide (95:5:0.5 v/v) as eluent afforded 74 mg of the analytical sample as a white solid: mp 197°–199° C.; FAB MS: 755 (M+H), 777 (M+Na); $^1$HNMR (DMSO-$D_6$): spectrum is in accord with the structure of the title compound.

Elemental analysis for $C_{40}H_{66}N_8O_6$: Calculated: C, 63.63; H, 8.81; N, 14.84. Found: C, 63.38; H, 8.80; N, 14.63.

EXAMPLE 2 cyclo-[D-3-Cyclohexylalanyl-L-isoleucyl-D-2,3,4,5-tetrahydro-3-pyidazinecarbonyl-L-2,3,4,5-tetrahydro-3-pyridazinecarbonyl-3-cyclohexyl-N-methyl-D-alanyl-L-prolyl]

An ice cold solution of cyclo-[D-3-cyclohexylalanyl-L-isoleucyl-D-hexahydro-3-pyridazinecarbonyl-L-hexahydro-3-pyridazinecarbonyl-3-cyclohexyl-N-methyl-D-alanyl-L-prolyl] (42 mg, 0.06 mmole) in 1 ml of dry pyridine was treated with 14 μL (0.132 mmole) of tert-butylhypochlorite. After one hour all volatiles were removed under reduced pressure and the residual semi-solid was purified via preparative thick layer chromatography on silica gel (2 mm plate thickness) using chloroform-methanol-concentrated ammonium hydroxide (95:5:0.5 v/v) as eluent. In this way, 38 mg of the analytical sample was obtained as a white solid: mp 122° C.; FAB MS: 751 (M+H), 773 (M+Na); $^1$HNMR (DMSO-$D_6$): spectrum is in accord with the structure of the title compound and confirms that the isolated material is a solvate.

Elemental analysis for $C_{40}H_{62}N_8O_6 \cdot 0.9CHCl_3$: Calculated: C, 57.22; H, 7.39; N, 13.07. Found: C, 57.38; H, 7.57; N, 13.05.

EXAMPLE 3 cyclo-[D-Phenylalanyl-L-isoleucyl-D-2,3,4,5-tetrahydro-3-pyridazinecarbonyl-L-hexahydro-6-oxo-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (100 mg, 0.13 mmole) was dissolved in 3 ml of ethanol and mixed with 30% aqueous hydrogen peroxide (50 μL, 0.44 mmole) and 0.5 ml of 1M sodium hydroxide solution. The reaction mixture was stirred at room temperature overnight. Additional quantities of 30% hydrogen peroxide and 1M sodium hydroxide solution were added as required to drive the reaction to completion (monitored by TLC and HPLC chromatography.) The reaction mixture was carefully concentrated in vacuo and the residual material was purified via preparative thick layer chromatography on silica gel (2 mm plate thickness) using chloroform-methanol-concentrated ammonium hydroxide (90:10:1 v/v) as eluent. In this way, 36 mg of the analytical sample was obtained as a solid: mp 134° C.; FAB MS: 755 (M+H), 777 (M+Na); $^1$HNMR (DMSO-D$_6$): spectrum is in accord with the structure of the title compound and confirms that the isolated material is a solvate.

Elemental analysis for $C_{40}H_{50}N_8O_7 \cdot 0.45CHCl_3 \cdot 2.1H_2O$: Calculated: C, 57.39; H, 6.51; N, 13.24. Found: C, 57.40; H, 6.52; N, 13.07.

EXAMPLE 4 cyclo-[D-Phenylalanyl-L-isoleucyl-D-hexahydro-3-pyridazinecarbonyl-L-hexahydro-6-oxo-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-L-hexahydro-6-oxo-3-pyridazinecarbonyl-N-methyl-D-phenylalanyl-L-prolyl] (92 mg, 0.12 mmole) was dissolved in 2 ml of glacial acetic acid and treated with 27 mg (0.43 mmole) of sodium cyanoborohydride at room temperature. After two hours, an additional mole equivalent of reducing reagent was added and the reaction mixture was stirred for 60 hours. The reaction mixture was filtered, concentrated under reduced pressure and the residue was purified via preparative thick layer chromatography on silica gel (2 mm plate thickness) using chloroform-methanol-concentrated ammonium hydroxide (90:10:1 v/v) as eluent. In this way, 65 mg of the analytical sample was obtained as a solid: mp 96° C.; FAB MS: 757 (M+H); $^1$HNMR (DMSO-D$_6$): spectrum is in accord with the structure of the title compound and confirms that the isolated material is a solvate.

Elemental analysis for $C_{40}H_{52}N_8O_7 \cdot 0.9CHCl_3$: Calculated: C, 56.83; H, 6.17; N, 12.97. Found: C, 57.01; H, 6.49; N, 12.92.

EXAMPLE 5 cyclo-[D-Phenylalanyl-L-isoleucyl-D-2,3,4,5-tetrahydro-3-pyidazinecarbonyl-L-2,3,4,5-tetrahydro-6-methylthio-3-pyridazinecarbonyl-N-methyl-D-phenylalanyl-L-prolyl]

To a solution of 3 ml of toluene containing 100 mg (0.13 mmole) of cyclo-[D-phenylalanyl-L-isoleucyl-D-2,3,4,5-tetrahydro-3-pyridazinecarbonyl-L-hexahydro-6-oxo-3-pyridazinecarbonyl-N-methyl-D-phenylalanyl-L-prolyl] was added 30 mg (0.07 mmole) of 2,3-bis(4-methoxyphenyl)-1,3-dithia-2,4-diphosphetane-2,4-disulfide (Lawesson's reagent). The reaction mixture was stirred at room temperature for 14 hours, diluted with 200 ml of chloroform and washed with 1M sodium hydroxide solution (2×40 ml). The organic phase was dried and concentrated to yield 146 mg of crude product. 60 mg of this material was combined with tetra-n-butylammonium-hydrogensulfate (10 mg), 0.5 ml methyliodide, 5 ml sodium hydroxide solution (20%), and 10 ml of toluene-tetrahydrofuran (1:1 v/v). The resulting reaction mixture was stirred vigorously for 2 hours, the phases were separated and the aqueous phase was extracted with toluene/tetrahydrofuran (1:1). The combined organic extracts were washed with brine, dried (sodium sulfate) and concentrated. The crude product was purified via preparative thick layer chromatography on silica gel (2 mm plate thickness) using chloroform-methanol-concentrated ammonium hydroxide (92:8:0.8 v/v) as eluent. In this way, 60 mg of the analytical sample was obtained as a solid: mp 107° C.; FAB MS: 785 (M+H), 807 (M+Na); $^1$HNMR (DMSO-D$_6$): spectrum is in accord with the structure of the title compound and confirms that the isolated material is a solvate.

Elemental analysis for $C_{41}H_{52}N_8O_6S \cdot 1.15CHCl_3 \cdot 0.2H_2O$: Calculated: C, 54.67; H, 5.83; N, 12.10. Found: C, 54.93; H, 5.94; N, 11.71.

EXAMPLE 6 cyclo-[D-Phenylalanyl-L-isoleucyl-D-hexahydro-1-methyl-3-pyridazinecarbonyl-L-hexahydro-1-methyl-3-pyridazinecarbonyl-N-methyl-D-phenylalanyl-L-prolyl]

A mixture of cyclo-[D-phenylalanyl-L-isoleucyl-D-hexahydro-3-pyridazinecarbonyl-L-hexahydro-3-pyridazinecarbonyl-N-methyl-D-phenylalanyl-L-prolyl] (93 mg, 0.13 mmole) and sodium cyanoborohydride (10 equivalents) in 2 ml of glacial acetic acid was treated with 0.5 ml of 37% aqueous formaldehyde solution. The resulting reaction mixture was stirred at room temperature overnight. All volatiles were removed under reduced pressure and the residual semi-solid was partitioned between ethyl acetate and water. The phases were separated and the aqueous phase was back-extracted with ethyl acetate. The combined organic extracts were washed with brine, dried and concentrated. Preparative thick layer chromatography on silica gel (2 mm plate thickness) using chloroform-methanol-concentrated ammonium hydroxide (96:4:0.4 v/v) as eluent afforded 23 mg of the analytical sample as a white solid: mp 105°-109° C.; FAB MS: 771 (M+H); $^1$HNMR (DMSO-D$_6$): spectrum is in accord with the structure of the title compound.

Elemental analysis for $C_{42}H_{58}N_8O_6 \cdot 0.95CHCl_3$: Calculated: C, 58.33; H, 6.72; N, 12.67. Found: C, 58.38; H, 6.55; N, 12.52.

EXAMPLE 7 cyclo-[N-(2-Amino-3-phenylpropyl)-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl]

A freshly prepared slurry of W-2 Raney-nickel (ca.2 g) was added to a solution of 104 mg of cyclo-[D-thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] in 50 ml of acetone. The resulting suspension was stirred vigorously and heated to reflux. After 14 hours, an additional 2 g of Raney nickel was added and heating was continued for 2 hours more. The reaction mixture was cooled and filtered through glass micropore filter paper. The filter cake was washed thoroughly with ethanol and the combined filtrates were rotoevaporated to yield 98 mg of crude product. Preparative thick layer chromatography on silica gel (0.5 mm plate thickness) using chloroform-methanol (96:4 v/v) as eluent afforded 50 mg of the title compound. Rechromatography of this material on silica gel (0.25 mm plate thickness) using chloroform-methanol (97:3 v/v) as eluent afforded the analytical sample as a white solid: mp 118°–121° C.; FAB MS: 725 (M+H); $^1$HNMR (DMSO-D$_6$): spectrum is in accord with the structure of the title compound.

Elemental analysis for C$_{40}$H$_{52}$N$_8$O$_5$.0.4CHCl$_3$.0.3-H$_2$O: Calculated: C, 62.36; H, 6.87; N, 14.40. Found: C, 62.37; H, 6.86; N, 14.43.

EXAMPLE 8 cyclo-[D-Phenylalanyl-L-isoleucyl-D-2,3,4,5-tetrahydro-3-pyridazinecarbonyl-L-2,3-dihydro-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (95 mg, 0.14 mmole) and 2,3-dichloro-5,6-dicyano-1,4-benzoquinone (68 mg, 0.30 mmole) were combined in 5 ml of benzene. The resulting mixture was heated at reflux for 16 hours. The reaction mixture was cooled, diluted with ethyl acetate (200 ml) and washed with 1M sodium hydroxide solution (3×25 ml) and brine. The combined organic extracts were dried (sodium sulfate) and concentrated. The crude product was purified via preparative thick layer chromatography on silica gel (2 mm plate thickness) using chloroform-methanol-concentrated ammonium hydroxide (90:10:1 v/v) as eluent. In this way, 36 mg of the title compound was obtained as a solid: mp 116° C.; FAB MS: 737 (M+H), 759 (M+Na); $^1$HNMR (DMSO-D$_6$): spectrum is in accord with the structure of the title compound and confirms that the isolated material is a solvate.

Elemental analysis for C$_{40}$H$_{48}$N$_8$O$_6$.0.35CHCl$_3$.2.2-H$_2$O: Calculated: C, 59.22; H, 6.50; N, 13.69. Found: C, 59.25; H, 6.51; N, 13.40.

EXAMPLE 9 cyclo-[D-Phenylalanyl-L-isoleucyl-D-2,3,4,5-tetrahydro-3-pyridazinecarbonyl-6-[[2-(1,1-dimethylethoxy)-2-oxoethyl]thio]-L-2,3,4,5-tetrahydro-3-pyridazine-carbonyl-N-methyl-D-phenylalanyl-L-prolyl]

To a solution of 3 ml of toluene containing 100 mg (0.13 mmole) of cyclo-[D-phenylalanyl-L-isoleucyl-D-2,3,4,5-tetrahydro-3-pyridazinecarbonyl-L-hexahydro-6-oxo-3-pyridazinecarbonyl-N-methyl-D-phenylalanyl-L-prolyl] was added 30 mg (0.07 mmole) of 2,3-bis(4-methoxyphenyl)-1,3-dithia-2,4-diphosphetane-2,4-disulfide (Lawesson's reagent). The reaction mixture was stirred at room temperature for 14 hours, diluted with 200 ml of chloroform and washed with 1M sodium hydroxide solution (2×40 ml). The organic phase was dried and concentrated to yield 146 mg of crude product. 98 mg of this material was combined with tetra-n-butylammonium-hydrogensulfate (34 mg), 27 μL (0.17 mmole) of tert-butylbromoacetate, 5 ml sodium hydroxide solution (20%), and 10 ml of toluenetetrahydrofuran (1:1 v/v). The resulting reaction mixture was stirred vigorously for 14 hours. More tert-butylbromoacetate (54 mL) was added to the reaction mixture, including also 30 mg (0.20 mmole) of sodium iodide. After three hours the phases were separated and the aqueous phase was extracted with chloroform. The combined organic extracts were washed with brine, dried (sodium sulfate) and concentrated. The reaction product was purified via preparative thick layer chromatography on silica gel (2 mm plate thickness) using chloroform-methanol-concentrated ammonium hydroxide (95:5:0.5 v/v) as eluent. In this way, 56 mg of the analytical sample was obtained as a solid: mp 104°–106° C.; FAB MS: 829 (M-isobutylene), 885 (M), 908 (M+Na); $^1$HNMR (DMSO-D$_6$): spectrum is in accord with the structure of the title compound and confirms that the isolated material is a solvate.

Elemental analysis for C$_{46}$H$_{60}$N$_8$O$_8$S.0.45CHCl$_3$: Calculated: C, 59.42; H, 6.49; N, 11.94. Found: C, 59.47; H, 6.48; N, 11.72.

EXAMPLE 10 cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (1.0 g, 1.35 mmole) and 2,3-bis(4-methoxyphenyl)-1,3-dithia-2,4-diphosphetane-2,4-disulfide (Lawesson's reagent) (191 mg, 0.35 molar equivalents) were combined in 40 ml of toluene. The resulting mixture was immersed in a preheated oil bath (95° C.) for one hour. A second portion of Lawesson's reagent was added (81 mg, 0.15 molar equivalents) and heating was continued for one hour more. The reaction mixture was cooled, diluted with 250 ml of chloroform, and washed with 1M sodium hydroxide solution (2×50 ml). The combined organic extracts were washed with brine, dried (sodium sulfate), and concentrated to yield 1.3 g of crude product. Chromatography on silica gel using chloroform-methanol-concentrated ammonium hydroxide (94:6:0.6 v/v) as eluent yielded 780 mg of the title compound as a solid. Recrystallization from absolute ethanol afforded the analytical sample: mp 225°–227° C.; FAB MS: 755 (M+H), 777 (M+Na); $^1$HNMR (DMSO-D$_6$): spectrum is in accord with the structure of the title compound.

Elemental analysis for C$_{40}$H$_{50}$N$_8$O$_5$S: Calculated: C, 63.63; H, 6.68; N, 14.84. Found: C, 63.95; H, 6.39; N, 14.76.

EXAMPLE 11 cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-thioprolyl]

cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (64 mg) was heated in toluene with 1.1 mole equivalents of 2,3-bis(4-methoxy-phenyl)-1,3-dithia-2,4-diphosphetane-2,4-disulfide (Lawesson's reagent) for 3 hours. The reaction mixture was cooled, diluted with 25 ml of chloroform, and washed with 1M sodium hydroxide solution (2×10 ml). The combined organic extracts were washed with brine, dried (sodium sulfate), and concentrated to yield the crude product. Chromatography on silica gel using chloroform-methanol-concentrated ammonium hydroxide (96:4:0.4 v/v) as eluent yielded the title compound as a solid: mp 219°–220° C.; FAB MS: 771 (M+H), 793 (M+Na); $^1$HNMR (DMSO-D$_6$): spectrum is in accord with the structure of the title compound and confirmed that it is a solvate.

Elemental analysis for C$_{40}$H$_{50}$N$_8$O$_4$S$_2$.0.75CHCl$_3$.0.15H$_2$O: Calculated: C, 56.59; H, 5.96; N, 12.98. Found: C, 56.89; H, 5.75; N, 12.59.

EXAMPLE 12 cyclo-[(R)-N-(2-amino-3-phenyl-1-(2-propenylthio)-propylidene)-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl]

cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (133 mg, 0.18 mmole) was combined with tetra-n-butylammoniumhydrogensulfate (30 mg), 19 μL (0.22 mmole) allylbromide, 5 ml sodium hydroxide solution (20%), and 10 ml of toluene-tetrahydrofuran (1:1 v/v). The resulting reaction mixture was stirred vigorously for 15 minutes, the phases were separated and the aqueous phase was extracted with toluene/tetrahydrofuran (1:1). The combined organic extracts were washed with brine, dried (sodium sulfate) and concentrated to yield 110 mg of the crude product. This material was purified via preparative thick layer chromatography on silica gel (2 mm plate thickness) using chloroform-methanol-concentrated ammonium hydroxide (97:3:0.3 v/v) as eluent. In this way, 72 mg of the analytical sample was obtained as a solid: mp 127°-130° C.; FAB MS: 795 (M+H); $^1$HNMR (DMSO-D$_6$): spectrum is in accord with the structure of the title compound and confirms that this material is a solvate.

Elemental analysis for $C_{41}H_{52}N_8O_6S \cdot 1.15CHCl_3 \cdot 0.2H_2O$: Calculated: C, 54.67; H, 5.83; N, 12.10. Found: C, 54.93; H, 5.94; N, 11.71.

EXAMPLE 13 cyclo-[D-Phenylalanyl-L-isoleucyl-D-2,3,4,5-tetrahydro-3-pyridazinecarbonyl-(3α,4β,5β)-4,5-dihydroxy-L-2,3,4,5-tetrahydro-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-L-2,3-dihydro-3-pyridazinecarbonyl-N-methyl-D-phenylalanyl-L-prolyl] (61 mg, 0.08 mmole) was dissolved in 3 ml of toluene containing 0.5 ml of pyridine. To this solution was added in one portion 30 mg (0.12 mmole) of osmium tetroxide. The resulting brown, heterogeneous reaction mixture was stirred at room temperature overnight. The volatiles were removed under reduced pressure and the residue was suspended in 15 ml of a water/ethanol mixture (2:1 v/v). Sodium bisulfite (200 mg) was added and the reaction mixture was heated to reflux for one hour. The black suspension was filtered and the filtrate was rotoevaporated to dryness. The residual material was dissolved in chloroform and purified via preparative thick layer chromatography on silica gel (2 mm plate thickness) using chloroform-methanol-concentrated ammonium hydroxide (89:11:1.1 v/v) as eluent. In this way, 39 mg of the title compound was obtained as a solid. Trituration with ether/petroleum ether gave the analytical sample: mp 161°-164° C.; FAB MS: 771 (M+H), 783 (M+Na); $^1$HNMR (DMSO-D$_6$): spectrum is in accord with the structure of the title compound and confirms that this material is a solvate.

Elemental analysis for $C_{40}H_{50}N_8O_8 \cdot 1.05H_2O$: Calculated: C, 60.82; H, 6.65; N, 14.19. Found: C, 60.83; H, 6.47; N, 13.89.

EXAMPLE 14 cyclo-[D-Phenylalanyl-L-isoleucyl-D-hexahydro-3-pyridazinecarbonyl-(3α,4β,5β)-4,5-dihydroxy-L-2,3,4,5-tetrahydro-3-pyridazinecarbonyl-N-methyl-D-phenylalanyl-L-prolyl]trifluoroacetate salt.

A solution of 1 ml glacial acetic acid containing 30 mg (0.039 mmole) = of cyclo-[D-phenylalanyl-L-isoleucyl-D-2,3,4,5-tetrahydro-3-pyridazinecarbonyl-(3α,4β,5β)-4,5-dihydroxy-L-2,3,4,5-tetrahydro-3-pyridazinecarbonyl-N-methyl-D-phenylalanyl-L-prolyl] was treated with 10 mg of sodium cyanoborohydride at room temperature. The reaction mixture was protected from moisture and stirred for two hours. More sodium cyanoborohydride (5 mg) was added and stirring was continued for 1 hour more. The reaction mixture was concentrated under reduced pressure and the residual material was purified via preparative thick layer chromatography on silica gel (2 mm plate thickness) using chloroform-methanol-concentrated ammonium hydroxide (87:13:1.3 v/v) as eluent. In this way, 30 mg of the title compound was obtained as a solid. Trituration with ether/petroleum ether gave a solid which was further purified by HPLC chromatography employing a one inch Vydac column and acetonitrile-trifluoroacetic acid-water as the mobile phase (8 ml/min). The analytical sample melted at 166°-169° C.; FAB MS: 773 (M+H), 795 (M+Na); $^1$HNMR (DMSO-D$_6$): spectrum is in accord with the structure of the title compound and confirms that this material is a solvate.

Elemental analysis for $C_{40}H_{52}N_8O_8 \cdot 0.05H_2O \cdot 1.0CF_3CO_2H$: Calculated: C, 56.30; H, 6.08; N, 12.51. Found: C, 56.29; H, 6.05; N, 12.65.

EXAMPLE 15 cyclo-[D-Phenylalanyl-L-isoleucyl-D-2,3,4,5-tetrahydro-3-pyridazinecarbonyl-5-(1-pyrolidinyl)-L-2,3,4,5-tetrahydro-3-pyridazinecarbonyl-N-methyl-D-phenylalanyl-L-prolyl] trifluoroacetate cyclo-[D-Phenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (755 mg, 1.02 mmole) and 200 mg (1.12 mmole) of recrystallized N-bromosuccinimide (NBS) were combined with 20 ml of carbon tetrachloride in a 100 ml roundbottom flask fitted with a reflux condenser. The resulting mixture was irradiated with a 250-Watt sunlamp for 1.5 hours during which time the solvent refluxed. More NBS (25 mg, 0.14 mmole) was added and the reaction was continued for an additional 45 minutes. The solvent was removed in vacuo and the dark-colored residue was chromatographed on silica gel employing chloroform-methanol-concentrated ammonium hydroxide (93:7:0.7 v/v) to afford 460 mg of cyclo-[D-phenylalanyl-L-isoleucyl-D-2,3,4,5-tetrahydro-3-pyridazinecarbonyl-5-(bromo)-L-2,3,4,5-tetrahydro-3-pyridazinecarbonyl-N-methyl-D-phenylalanyl-L-prolyl]. Trituration with acetone gave the analytical sample.

Pyrrolidine (195 μL, 2.33 mmole) and 870 mg (1.06 mmole) of cyclo-[D-phenylalanyl-L-isoleucyl-D-2,3,4,5-tetrahydro-3-pyridazinecarbonyl-5-(bromo)-L-2,3,4,5,-tetrahydro-3-pyridazinecarbonyl-N-methyl-D-phenylalanyl-L-prolyl] were combined in 15 ml of dry tetrahydrofuran. The resulting solution was stirred at room temperature for 23 hours. All volatiles were removed in vacuo to yield approximately 900 mg of a foam. This material was purified via preparative TLC chromatography on silica gel plates (0.5 mm thickness) employing chloroform-methanol-concentrated ammonium hydroxide (92:8:0.8 v/v) to afford two major fractions. The lower $R_f$ fraction (156 mg) was further purified by preparative reverse phase HPLC on a Vydac column (1", acetonitrile:water:trifluoroacetic acid mobile phase, 8 ml/min) to yield the title compound as a solid: mp 115°-118° C.; FAB MS: 808 (M+H); $^1$HNMR (DMSO-D$_6$): spectrum is in accord with the structure of the title compound and confirms that this material is a solvate.

Elemental analysis for $C_{44}H_{57}N_9O_6 \cdot 2.05CHCl_3 \cdot 1.0CF_3CO_2H$: Calculated: C, 50.86; H, 5.33; N, 11.11. Found: C, 50.93; H, 5.11; N, 11.04.

EXAMPLE 16 cyclo-[D-Phenylalanyl-L-isoleucyl-D-2,3,4,5-tetrahydro-3-pyridazinecarbonyl-5-((2-dimethylamino)ethylamino)-L-2,3,4,5,-tetrahydro-3-pyridazinecarbonyl-N-methyl-D-phenylalanyl-L-prolyl] (trifluoroacetate) (High $R_f$ isomer)

To a solution of 2 ml of N,N-dimethyl-formamide containing 400 mg (0.49 mmole) of cyclo-[D-phenylalanyl-L-isoleucyl-D-2,3,4,5-tetrahydro-3-pyridazinecarbonyl-5-(bromo)-L-2,3,4,5,-tetrahydro-3-pyridazinecarbonyl-N-methyl-D-phenylalanyl-L-prolyl] (prepared according to the procedure set forth in Example 15) was added 161 μL (1.47 mmole) of N,N-dimethylaminoethylamine. The resulting solution was protected from moisture and stirred at room temperature overnight. All volatiles were removed under reduced pressure and the residual material was purified via preparative TLC chromatography on silica gel plates (0.5 mm thickness) employing chloroform-methanol-concentrated ammonium hydroxide (90:10:1 v/v) to afford two major fractions. The higher $R_f$ fraction (47 mg) was further purified by preparative reverse phase HPLC on a Vydac column (1", acetonitrile:water:trifluoroacetic acid mobile phase, 8 ml/min) to yield the title compound as a solid: mp 117°-120° C.; FAB MS: 825 (M); $^1$HNMR (DMSO-D$_6$): spectrum is in accord with the structure of the title compound and confirms that this material is a solvate.

Elemental analysis for $C_{44}H_{60}N_{10}O_6 \cdot 0.05H_2O \cdot 2.4CF_3CO_2H$: Calculated: C, 50.86; H, 5.33; N, 11.11. Found: C, 50.93; H, 5.11; N, 11.04.

EXAMPLE 17 cyclo-[D-Phenylalanyl-L-isoleucyl-D-2,3,4,5-tetrahydro-3-pyridazinecarbonyl-5-(2-ethoxy-1-(ethoxycarbonyl)-2-oxoethyl)-L-2,3,4,5,-tetrahydro-3-pyridazinecarbonyl-N-methyl-D-phenylalanyl-L-prolyl] (trifluoroacetate)

A 0.23 molar solution of sodium ethoxide in ethanol (10.4 ml, 2.4 mmole) was added under an inert atmosphere to 352 μL (2.32 mmole) of diethylmalonate in 1 ml of ethanol. The mixture was stirred for 15 minutes, cooled to 0° C., and treated with an ethanolic solution of 1.27 g (1.55 mmole) of cyclo-[D-phenylalanyl-L-isoleucyl-D-2,3,4,5-tetrahydro-3-pyridazinecarbonyl-5-(bromo)-L-2,3,4,5,-tetrahydro-3-pyridazinecarbonyl-N-methyl-D-phenylalanyl-L-prolyl] (prepared according to the procedure set forth in Example 15). The resulting solution was stirred initially at 0° C. and then was warmed to room temperature over the course of several hours. After a total reaction time of 48 hours the reaction mixture was rotoevaporated. The residual material was chromatographed on silica gel employing chloroform-methanol-concentrated ammonium hydroxide (98:2:0.2 v/v) to afford a mixture of two diastereomers (757 mg). Further processing of the chromatographed material via preparative reverse phase HPLC on a Vydac column (1", acetonitrile:water:trifluoroacetic acid mobile phase, 8 ml/min) gave the title compound as a solid: mp 77°-80° C.; FAB MS: 897 (M+H); $^1$HNMR (DMSO-D$_6$): spectrum is in accord with the structure of the title compound and confirms that this material is a solvate.

Elemental analysis for $C_{47}H_{60}N_8O_{10} \cdot 1.05H_2O \cdot 0.85CF_3CO_2H$: Calculated: C, 57.74; H, 6.26; N, 11.06. Found: C, 57.74; H, 6.23; N, 11.14.

EXAMPLE 18 cyclo-[D-Phenylalanyl-L-isoleucyl-D-2,3,4,5-tetrahydro-3-pyridazinecarbonyl-trans-5-(dimethylamino)-methyl-L-2,3,4,5,-tetrahydro-3-pyridazinecarbonyl-N-methyl-D-phenylalanyl-L-prolyl] monoacetate N,N-Dimethylmethyleneammonium iodide 20 g (108 mmole) was suspended in 75 ml of dry tetrahydrofuran under an inert atmosphere and stirred. The supernatant liquid was decanted and the residual solid was resuspended in tetrahydrofuran. This cycle was repeated twice more. The resulting decolorized salt was suspended in 100 ml of tetrahydrofuran and treated with a solution of cyclo-[D-phenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl] (5.01 g, 6.79 mmole) in 35 ml of tetrahydrofuran. To this solution was added 10-camphorsulfonic acid (0.7 g, 3 mmole) and the resulting reaction mixture was refluxed for five hours. Analysis by HPLC of an aliquot indicated circa 50% conversion of the starting material to products. The reaction mixture was cooled, diluted with ethyl acetate (250 ml), and washed in succession with saturated sodium bicarbonate solution (2×250 ml) and sodium sulfite solution (2×150 ml). The aqueous washings were back-extracted with ethyl acetate and the combined organic extracts were dried (magnesium sulfate) and concentrated under reduced pressure. The residual material was column chromatographed on silica gel employing chloroform-methanol-concentrated ammonium hydroxide (gradient from 95:5:0.5 to 90:10:1 v/v) to afford the free base of the title compound as a white foam. The acetate salt was obtained by lyophilization of the latter compound from a solution of 5% aqueous acetic acid: FAB MS: 796 (M+H); $^1$HNMR (DMSO-D$_6$ plus CF$_3$CO$_2$D): spectrum is in accord with the structure of the title compound and confirms that this material is a solvate.

Elemental analysis for $C_{43}H_{57}N_9O_6 \cdot 1.0CH_3CO_2H$: Calculated: C, 63.14; H, 7.18; N, 14.73. Found: C, 63.00; H, 7.04; N, 14.90.

EXAMPLE 19 cyclo-[D-Thiophenylalanyl-L-isoleucyl-D-2,3,4,5-tetrahydro-3-pyridazinecarbonyl-5-methylene-L-2,3,4,5-tetrahydro-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-trans-5-(dimethylamino)methyl-L-2,3,4,5,-tetrahydro-3- pyridazinecarbonyl-N-methyl-D-phenylalanyl-L-prolyl] (95 mg, 0.12 mmole) and 2,3-bis(4-methoxyphenyl)-1,3-dithia-2,4-diphosphetane-2,4-disulfide (Lawesson's reagent) (24 mg, 06 mmole) were combined in 3 ml of toluene. The resulting mixture was immersed in a preheated oil bath (80° C.) for 24 hours. A second portion of Lawesson's reagent was added (5 mg) and heating was continued at 90°-100° C. for 31 hours. The reaction mixture was cooled, diluted with 10 ml of chloroform, and washed with 1M sodium hydroxide solution (2×5 ml). The combined organic extracts were washed with brine, dried (sodium sulfate), and concentrated. The crude reaction product was applied directly to preparative silica gel plates and developed with chloroform-methanol-concentrated ammonium hydroxide (95:5:0.5 v/v). The reaction component with an $R_f$ value of 0.3 was isolated and triturated with ethanol/petroleum ether to give 4.4 mg of the analytical sample of the title compound: mp 217° C.; FAB MS: 767 (M+H); $^1$HNMR (DMSO-D$_6$): spectrum is in accord with the structure of the title compound.

Elemental analysis for $C_{41}H_{50}N_8O_5S.0.25CHCl_3.0.6 H_2O$: Calculated: C, 61.34; H, 6.42; N, 13.88. Found: C, 61.32; H, 6.43; N, 14.09.

EXAMPLE 20 cyclo-[D-Phenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl]

cyclo-[D-Phenylalanyl-L-isoleucyl-D-2,3,4,5-tetrahydro-3-pyridazinecarbonyl-trans-5-(dimethylamino)methyl-L-2,3,4,5,-tetrahydro-3-pyridazinecarbonyl-N-methyl-D-phenylalanyl-L-prolyl] (95 mg, 0.12 mmole) and 2,3-bis(4-methoxyphenyl)-1,3-dithia-2,4-diphosphetane-2,4-disulfide (Lawesson's reagent) (24 mg, 06 mmole) were combined in 3 ml of toluene. The resulting mixture was immersed in a preheated oil bath (80° C.) for 24 hours. A second portion of Lawesson's reagent was added (5 mg) and heating was continued at 90°-100° C. for 31 hours. The reaction mixture was cooled, diluted with 10 ml of chloroform, and washed with 1M sodium hydroxide solution (2×5 ml). The combined organic extracts were washed with brine, dried (sodium sulfate), and concentrated. The crude reaction product was applied directly to preparative silica gel plates and developed with chloroform-methanol-concentrated ammonium hydroxide (95:5:0.5 v/v). The reaction component with an $R_f$ value of 0.15 was isolated and triturated with diethyl ether/petroleum ether to give 3.0 mg of the analytical sample of the title compound: mp 167° C.; FAB MS: 751 (M), 773 (M+Na); $^1$HNMR (DMSO-D$_6$): spectrum is in accord with the structure of the title compound.

Elemental analysis for $C_{41}H_{50}N_8O_6.1.7CHCl_3.1.8 H_2O$: Calculated: C, 52.00; H, 5.65; N, 11.36. Found: C, 51.73; H, 5.35; N, 11.76.

The following are preferred compounds of the invention:

cyclo-[D-3-Cyclohexylalanyl-L-isoleucyl-D-hexahydro-3-pyridazinecarbonyl-L-hexahydro-3-pyridazinecarbonyl-3-cyclohexyl-N-methyl-D-alanyl-L-prolyl];

cyclo-[D-3-Cyclohexylalanyl-L-isoleucyl-D-2,3,4,5-tetrahydro-3-pyridazinecarbonyl-L-2,3,4,5-tetrahydro-3-pyridazinecarbonyl-3-cyclohexyl-N-methyl-D-alanyl-L-prolyl];

cyclo-[D-Phenylalanyl-L-isoleucyl-D-2,3,4,5-tetrahydro-3-pyridazinecarbonyl-L-hexahydro-6-oxo-3-pyridazine-carbonyl-N-methyl-D-phenylalanyl-L-prolyl];

cyclo-[D-Phenylalanyl-L-isoleucyl-D-hexahydro-3-pyridazinecarbonyl-L-hexahydro-6-oxo-3-pyridazine-carbonyl-N-methyl-D-phenylalanyl-L-prolyl];

cyclo-[D-Phenylalanyl-L-isoleucyl-D-2,3,4,5-tetrahydro-3-pyridazinecarbonyl-L-2,3,4,5-tetrahydro-6-methylthio-3-pyridazinecarbonyl-N-methyl-D-phenylalanyl-L-prolyl];

cyclo-[D-Phenylalanyl-L-isoleucyl-D-hexahydro-1-methyl-3-pyridazinecarbonyl-L-hexahydro-1-methyl-3-pyridazinecarbonyl-N-methyl-D-phenylalanyl-L-prolyl];

cyclo-[N-(2-amino-3-phenylpropyl)-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl];

cyclo-[D-Phenylalanyl-L-isoleucyl-D-2,3,4,5-tetrahydro-3-pyridazinecarbonyl-L-2,3-dihydro-3-pyridazine-carbonyl-N-methyl-D-phenylalanyl-L-prolyl];

cyclo-[D-Phenylalanyl-L-isoleucyl-D-2,3,4,5-tetrahydro-3-pyridazinecarbonyl-6-[[2-(1,1-dimethylethoxy)-2-oxoethyl]thio]-L-2,3,4,5-tetrahydro-3-pyridazine-carbonyl-N-methyl-D-phenylalanyl-L-prolyl];

cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl];

cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-thioprolyl];

cyclo-[(R)-N-(2-amino-3-phenyl-1-(2-propenylthio)-propylidene)-L-isoleucyl-D-2,3,4,5-tetrahydro-3-pyridazinecarbonyl-L-2,3,4,5-tetrahydro-3-pyridazine-carbonyl-N-methyl-D-phenylalanyl-L-prolyl];

cyclo-[D-Phenylalanyl-L-isoleucyl-D-2,3,4,5-tetrahydro-3-pyridazinecarbonyl-(3α,4β,5β)-4,5-dihydroxy-L-2,3,4,5-tetrahydro-3-pyridazinecarbonyl-N-methyl-D-phenylalanyl-L-prolyl];

cyclo-[D-Phenylalanyl-L-isoleucyl-D-hexahydro-3-pyridazinecarbonyl-(3α,4β,5β)-4,5-dihydroxy-L-2,3,4,5,-tetrahydro-3-pyridazinecarbonyl-N-methyl-D-phenylalanyl-L-prolyl]trifluoroacetate;

cyclo-[D-Phenylalanyl-L-isoleucyl-D-2,3,4,5-tetrahydro-3-pyridazinecarbonyl-5-(1-pyrolidinyl)-L-2,3,4,5,-tetrahydro-3-pyridazinecarbonyl-N-methyl-D-phenylalanyl-L-prolyl]trifluoroacetate;

cyclo-[D-Phenylalanyl-L-isoleucyl-D-2,3,4,5-tetrahydro-3-pyridazinecarbonyl-5-((2-dimethylamino)ethylamino)-L-2,3,4,5,-tetrahydro-3-pyridazinecarbonyl-N-methyl-D-phenylalanyl-L-prolyl]trifluoroacetate (High Rf isomer);

cyclo-[D-Phenylalanyl-L-isoleucyl-D-2,3,4,5-tetrahydro-3-pyridazinecarbonyl-5-(2-ethoxy-1-(ethoxy-carbonyl)-2-oxoethyl)-L-2,3,4,5,-tetrahydro-3-pyridazine-carbonyl-N-methyl-D-phenylalanyl-L-prolyl]-trifluoroacetate;

cyclo-[D-Phenylalanyl-L-isoleucyl-D-2,3,4,5-tetrahydro-3-pyridazinecarbonyl-trans-5-(dimethylamino)-methyl-L-2,3,4,5,-tetrahydro-3-pyridazinecarbonyl-N-methyl-D-phenylalanyl-L-prolyl]monoacetate;

cyclo-[D-Thiophenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl]; or cyclo-[D-Phenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl].

More preferred compounds of the invention are:
cyclo-[D-Phenylalanyl-L-isoleucyl-D-2,3,4,5-tetrahydro-3-pyridazinecarbonyl-L-hexahydro-6-oxo-3-pyridazine-carbonyl-N-methyl-D-phenylalanyl-L-prolyl];

cyclo-[D-Phenylalanyl-L-isoleucyl-D-2,3,4,5-tetrahydro-3-pyridazinecarbonyl-L-2,3-dihydro-3-pyridazine-carbonyl-N-methyl-D-phenylalanyl-L-prolyl];

cyclo-[D-Thiophenylalanyl-L-N-isoleucyl-D-2,3,4,5-tetrahydro-3-pyridazinecarbonyl-L-2,3,4,5-tetrahydro-3-pyridazinecarbonyl-N-methyl-D-phenylalanyl-L-thioprolyl];

cyclo-[D-Thiophenylalanyl-L-N-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl];

cyclo-[D-Thiophenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl]; or cyclo-[D-Phenylalanyl-L-isoleucyl-D-2,3,4,5-tetrahydro-3-pyridazinecarbonyl-trans-5-(dimethylamino)-methyl-L-2,3,4,5,-tetrahydro-3-pyridazinecarbonyl-N-methyl-D-phenylalanyl-L-prolyl]monoacetate.

RADIOLIGAND BINDING ASSAYS

The high affinity binding of [³H]OT ([tyrosyl, 3,5-[³H]OT; 30–60 Ci/mmol; New England Nuclear Boston, Mass.) to uterine OT receptors was based on an assay* using a crude membrane preparation of uteri taken from diethylstilbestrol dipropionate (DES)-treated (0.3 mg/kg, ip; 18–24) rats. Competition studies were conducted at equilibrium (60 min; 22° C.) using 1 nM [³H]OT in the following assay buffer: 50 mM Tris-HCl, 5 mM MgCl₂, and 0.1% BSA, pH 7.4. Nonspecific binding (10% of the total binding) was determined using 1 μM unlabeled OT and the binding reaction was terminated by filtration through glass fiber filters using a cell harvester (model 7019, Skatron, Inc., Sterling, Va.).

*Fuchs, A-R; Fuchs, F; Soloff, MS. 1985 J. Clin. Endocrinol. Metab. 60:37.

The measurement of [³H]AVP ([phenylalanyl-3,4,5-³H]AVP; 80–90 Ci/mmol; New England Nuclear) binding to a crude membrane preparation of male rat liver (AVP-V₁ sites) or kidney medulla (AVP-V₂ sites) was determined according to the method of Butlen et al+. Competition assays were conducted at equilibrium (30 min at 30° C.) using 1 nM [³H]AVP (liver) or 2 nM) [³H]AVP (kidney) in the following assay buffer: 100 mM Tris-HCl, 5 mM MgCl₂, 0.1% BSA, 50 μM phenylmethylsulfonylfluoride, and 50 μg/ml bactracin, pH 8.0. Nonspecific binding (5–10% of the total binding) was determined using 10 μM unlabeled AVP, and the binding reaction was terminated by filtration as described above for the [³H]OT binding assay.

+Butlen, D; Guillon, G; Rajerison, RM; Jard, S; Sawyer, WH; Manning, M. 1978 Mol Pharmacol 14:1006.

$K_i$ values were obtained for each compound from three to six separate determinations of the IC₅₀ values ($K_i$=IC₅₀/1+c/$K_d$)# using $K_d$ values obtained from saturation binding assay: [³H]OT (uterus), 0.7 nM; [³H]AVP (liver), 0.4 nM; [³H]AVP (kidney), 1.4 nM.

Table I shows receptor binding data for compounds prepared in Examples 1–20.

Cheng, Y-C; Prusoff, WH; 1973 Biochem Pharmacol 22:3099.

TABLE 1

| Compound of Example | Receptor Binding Results IC₅₀ (nM)* | | |
|---|---|---|---|
| | [3H]OT | [³H]-AVP-V₁ | [³H]-AVP-V₂ |
| 1 | 725 | 2,400 | 14,800 |
| 2 | 94 | ND* | ND |
| 3 | 20 | 4,700 | 17,000 |
| 4 | 217 | 13,900 | 18,900 |
| 5 | 27 | 820 | 1,020 |
| 6 | 6,245 | ND | ND |
| 7 | 30,000 | >30,000 | >30,000 |
| 8 | 20 | 1,415 | 1,350 |
| 9 | 564 | 10,000 | 10,000 |
| 10 | 1.0 | 300 | 270 |
| 11 | 4.9 | 200 | 430 |
| 12 | 710 | >10,000 | >10,000 |
| 13 | 785 | 10,000 | >10,000 |
| 14 | 290 | 10,000 | >10,000 |
| 15 | 600 | 8,800 | 11,000 |
| 16 | 220 | 930 | 7,300 |
| 17 | 200 | 3,000 | 2,400 |
| 18 | 7.8 | 1,850 | 2,800 |
| 19 | 3.6 | >1,000 | >1,000 |
| 20 | 37 | >10,000 | >10,000 |

ND = Not Determined
*Inhibition is expressed as IC₅₀ in nM. The IC₅₀ is the concentration of the test compound which inhibits specific binding by 50%.

What is claimed is:

1. A compound having the formula:

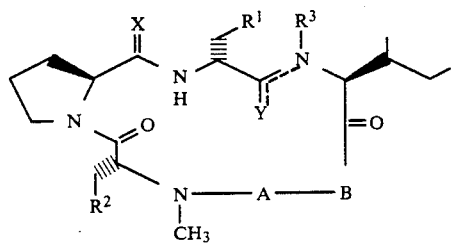

wherein:

A is 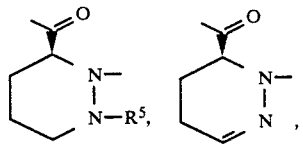

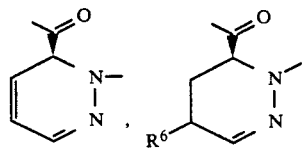

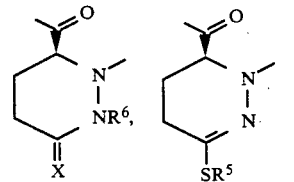

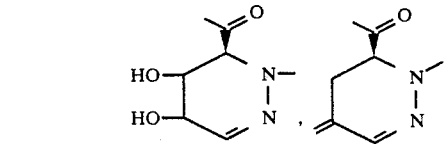

-continued

B is 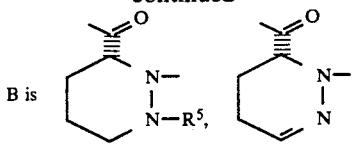

$R^1$ and $R^2$ are the same and are cyclohexyl or phenyl;
$R^3$ is hydrogen, $C_{1-4}$alkyl, or acetyl, when Y is O, S or $H_2$ for

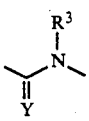

or $R^3$ is absent when Y is $S-C_{1-4}$alkyl or $SCH_2CO_2R^4$ for

$R^4$ is hydrogen, $C_{1-4}$ straight or branch chained alkyl;
$R^5$ is hydrogen except when attached to S, $C_{1-4}$alkyl, $CH_2CO_2R^4$;
$R^6$ is

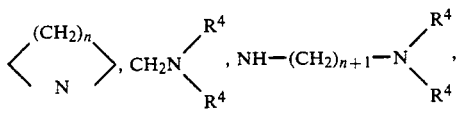

or $CH(CO_2R^4)_2$, where $R^4 \neq H$ and n is 1–4;
X is O or S;
Y is O, S, $H_2$, $S-C_{1-4}$alkyl or $S-CH_2-CO_2R^4$;
and the pharmaceutically acceptable salts thereof.

2. The compounds of claim 1 wherein:
$R^3$ is hydrogen;
$R^4$ is methyl or ethyl;
$R^5$ is hydrogen except when attached to S, or methyl; and
Y is O, S, or $H_2$.

3. The compounds of claim 1 which are:
cyclo-[D-3-Cyclohexylalanyl-L-isoleucyl-D-hexahydro-3-pyridazinecarbonyl-L-hexahydro-3-pyridazinecarbonyl-3-cyclohexyl-N-methyl-D-alanyl-L-prolyl];
cyclo-[D-3-Cyclohexylalanyl-L-isoleucyl-D-2,3,4,5-tetrahydro-3-pyridazinecarbonyl-L-2,3,4,5-tetrahydro-3-pyridazinecarbonyl-3-cyclohexyl-N-methyl-D-alanyl-L-prolyl];
cyclo-[D-Phenylalanyl-L-isoleucyl-D-2,3,4,5-tetrahydro-3-pyridazinecarbonyl-L-hexahydro-6-oxo-3-pyridazine-carbonyl-N-methyl-D-phenylalanyl-L-prolyl];
cyclo-[D-Phenylalanyl-L-isoleucyl-D-hexahydro-3-pyridazinecarbonyl-L-hexahydro-6-oxo-3-pyridazine-carbonyl-N-methyl-D-phenylalanyl-L-prolyl];
cyclo-[D-Phenylalanyl-L-isoleucyl-D-2,3,4,5-tetrahydro-3-pyridazinecarbonyl-L-2,3,4,5-tetrahydro-6-methylthio-3-pyridazinecarbonyl-N-methyl-D-phenylalanyl-L-prolyl];
cyclo-[D-3-Phenylalanyl-L-isoleucyl-D-hexahydro-1-methyl-3-pyridazinecarbonyl-L-hexahydro-1-methyl-3-pyridazinecarbonyl-N-methyl-D-phenylalanyl-L-prolyl];
cyclo-[N-(2-amino-3-phenylpropyl)-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl];
cyclo-[D-Phenylalanyl-L-isoleucyl-D-2,3,4,5-tetrahydro-3-pyridazinecarbonyl-L-2,3-dihydro-3-pyridazine-carbonyl-N-methyl-D-phenylalanyl-L-prolyl];
cyclo-[D-Phenylalanyl-L-isoleucyl-D-2,3,4,5-tetrahydro-3-pyridazinecarbonyl-6-[[2-(1,1-dimethylethoxy)-2-oxoethyl]thio]-L-2,3,4,5-tetrahydro-3-pyridazine-carbonyl-N-methyl-D-phenylalanyl-L-prolyl];
cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl];
cyclo-[D-Thiophenylalanyl-L-isoleucyl-D-2,3,4,5-tetrahydro-3-pyridazinecarbonyl-L-2,3,4,5-tetrahydro-3-pyridazinecarbonyl-N-methyl-D-phenylalanyl-L-thioprolyl];
cyclo-[(R)-N-(2-amino-3-phenyl-1-(2-propenylthio)-propylidene)-L-isoleucyl-D-2,3,4,5-tetrahydro-3-pyridazinecarbonyl-L-2,3,4,5-tetrahydro-3-pyridazine-carbonyl-N-methyl-D-phenylalanyl-L-prolyl];
cyclo-[D-Phenylalanyl-L-isoleucyl-D-2,3,4,5-tetrahydro-3-pyridazinecarbonyl-(3α,4β,5β)-4,5-dihydroxy-L-2,3,4,5,-tetrahydro-3-pyridazinecarbonyl-N-methyl-D-phenylalanyl-L-prolyl];
cyclo-[D-Phenylalanyl-L-isoleucyl-D-hexahydro-3-pyridazinecarbonyl-(3α,4β,5β)-4,5-dihydroxy-L-2,3,4,5,-tetrahydro-3-pyridazinecarbonyl-N-methyl-D-phenylalanyl-L-prolyl]trifluoroacetate;
cyclo-[D-Phenylalanyl-L-isoleucyl-D-2,3,4,5-tetrahydro-3-pyridazinecarbonyl-5-(1-pyrolidinyl)-L-2,3,4,5,-tetrahydro-3-pyridazinecarbonyl-N-methyl-D-phenylalanyl-L-prolyl]trifluoroacetate;
cyclo-[D-Phenylalanyl-L-isoleucyl-D-2,3,4,5-tetrahydro-3-pyridazinecarbonyl-5-((2-dimethylamino)ethylamino)-L-2,3,4,5,-tetrahydro-3-pyridazinecarbonyl-N-methyl-D-phenylalanyl-L-prolyl](trifluoroacetate) (High Rf isomer);
cyclo-[D-Phenylalanyl-L-isoleucyl-D-2,3,4,5-tetrahydro-3-pyridazinecarbonyl-5-(2-ethoxy-1-(ethoxy-carbonyl)-2-oxoethyl)-L-2,3,4,5,-tetrahydro-3-pyridazine-carbonyl-N-methyl-D-phenylalanyl-L-prolyl](trifluoroacetate);
cyclo-[D-Phenylalanyl-L-isoleucyl-D-2,3,4,5-tetrahydro-3-pyridazinecarbonyl-trans-5-(dimethylamino)methyl-L-2,3,4,5,-tetrahydro-3-pyridazinecarbonyl-N-methyl-D-phenylalanyl-L-prolyl]monoacetate;
cyclo-[D-Thiophenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl]; or
cyclo-[D-Phenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl].

4. The compounds of claim 3 which are:
cyclo-[D-Phenylalanyl-L-isoleucyl-D-2,3,4,5-tetrahydro-3-pyridazinecarbonyl-L-hexahydro-6-oxo-3-pyridazine-carbonyl-N-methyl-D-phenylalanyl-L-prolyl];

cyclo-[D-Phenylalanyl-L-isoleucyl-D-2,3,4,5-tetrahydro-3-pyridazinecarbonyl-L-2,3-dihydro-3-pyridazine-carbonyl-N-methyl-D-phenylalanyl-L-prolyl];

cyclo-[D-Thiophenylalanyl-L-N-isoleucyl-D-2,3,4,5-tetrahydro-3-pyridazinecarbonyl-L-2,3,4,5-tetrahydro-3-pyridazinecarbonyl-N-methyl-D-phenylalanyl-L-thioprolyl];

cyclo-[D-Thiophenylalanyl-L-N-isoleucyl-D-2,3,4,5-tetrahydro-3-pyridazinecarbonyl-L-2,3,4,5-tetrahydro-3-pyridazinecarbonyl-N-methyl-D-phenylalanyl-L-prolyl];

cyclo-[D-Thiophenylalanyl-L-isoleucyl-D-2,3,4,5-tetrahydro-3-pyridazinecarbonyl-5-methylene-L-2,3,4,5,-tetrahydro-3-pyridazinecarbonyl-N-methyl-D-phenylalanyl-L-prolyl]; or cyclo-[D-Phenylalanyl-L-isoleucyl-D-2,3,4,5-tetrahydro-3-pyridazinecarbonyl-trans-5-(dimethylamino)methyl-L-2,3,4,5,-tetrahydro-3-pyridazinecarbonyl-N-methyl-D-phenylalanyl-L-prolyl]monoacetate.

5. A method of antagonizing the binding of oxytocin to an oxytocin receptor which comprises contacting said receptor with a compound of claim 1.

6. A method of treating preterm labor or dysmenorrhea which comprises administering a pharmaceutically effective amount of a compound of claim 1.

7. A method of stopping labor prepatory to Caesarian delivery which comprises administering a pharmaceutically effective amount of a compound of claim 1.

8. A pharmaceutical composition which comprises a therapeutically effective amount of a compound of claim 1 and a pharmaceutically acceptable carrier.

* * * * *